US011959785B2

(12) United States Patent
Laumann

(10) Patent No.: US 11,959,785 B2
(45) Date of Patent: Apr. 16, 2024

(54) SYSTEM AND METHOD FOR MEASURING A MULTIPHASE FLOW BY MEASURING DENSITY AND ELECTRICAL IMPEDANCE FOR CORRECTING THE MEASUREMENT DUE TO EFFECT OF DEPOSITS ON INNER SURFACE OF PIPE WALLS

(71) Applicant: Roxar Flow Measurement AS, Stavanger (NO)

(72) Inventor: Dag Erik Laumann, Bergen (NO)

(73) Assignee: Roxar Flow Measurement AS, Stavanger (NO)

( * ) Notice: Subject to any disclaimer, the term of this patent is extended or adjusted under 35 U.S.C. 154(b) by 288 days.

(21) Appl. No.: 17/437,515

(22) PCT Filed: May 6, 2020

(86) PCT No.: PCT/EP2020/062502
§ 371 (c)(1),
(2) Date: Sep. 9, 2021

(87) PCT Pub. No.: WO2020/225274
PCT Pub. Date: Nov. 12, 2020

(65) Prior Publication Data
US 2022/0146291 A1 May 12, 2022

(30) Foreign Application Priority Data
May 7, 2019 (NO) .................................. 20190578

(51) Int. Cl.
*G01F 1/74* (2006.01)
*G01F 1/58* (2006.01)
*G01N 27/08* (2006.01)

(52) U.S. Cl.
CPC ............... *G01F 1/584* (2013.01); *G01F 1/74* (2013.01); *G01N 27/08* (2013.01)

(58) Field of Classification Search
None
See application file for complete search history.

(56) References Cited

U.S. PATENT DOCUMENTS

| 6,182,504 B1 | 2/2001 | Gaisford |
| 8,525,534 B2 * | 9/2013 | Brandt ..................... G01F 1/74 |
| | | 324/724 |

(Continued)

FOREIGN PATENT DOCUMENTS

| EP | 3058356 A1 | 8/2016 |
| GB | 2246866 A | 2/1992 |

(Continued)

OTHER PUBLICATIONS

Williams J: "Spe 28515 Status of Multiphase Flow Measurement Research", Spe Papers, XX, XX, Sep. 25, 1994 (Sep. 25, 1994), pp. 545-554, XP000749290.

(Continued)

*Primary Examiner* — Jamel E Williams
(74) *Attorney, Agent, or Firm* — Bradley Arant Boult Cummings LLP

(57) ABSTRACT

A method for measuring conditions in a pipe includes measuring a chosen electrical characteristic in the flow, measuring the density in essentially the same flow volume, and calculating a curve representing the relationship between the density and the electrical characteristic. The method further includes at least one of calculating the derivative of the curve, indicating the water to liquid ratio of the flow volume, and extrapolating the curve to the value representing density at no liquid, the value of the electric characteristic representing the characteristic of a possible deposit layer on the inner surface of the pipe.

19 Claims, 3 Drawing Sheets

(56) References Cited

U.S. PATENT DOCUMENTS

| 9,759,646 B2* | 9/2017 | Oikonomou ....... G01N 33/1833 |
| 2014/0331783 A1 | 11/2014 | Xie |
| 2015/0316402 A1 | 11/2015 | Wee et al. |
| 2016/0216196 A1* | 7/2016 | Oikonomou ............ G01F 1/712 |

FOREIGN PATENT DOCUMENTS

| JP | 2007-000840 A | 1/2007 |
| NO | 304332 B1 | 11/1998 |
| WO | WO-9403802 A1 | 2/1994 |
| WO | WO-0165212 A1 | 9/2001 |
| WO | WO-2005057142 A1 | 6/2005 |
| WO | WO-2007018434 A1 | 2/2007 |
| WO | WO-2008085065 A1 | 7/2008 |
| WO | WO-2015055767 A1 | 4/2015 |
| WO | WO-2016042317 A1 | 3/2016 |

OTHER PUBLICATIONS

Ruchaud, Nicolas; International Search Report; PCT/EP2020/062502; dated Nov. 25, 2020; 8 pages.

* cited by examiner

SYSTEM AND METHOD FOR MEASURING A MULTIPHASE FLOW BY MEASURING DENSITY AND ELECTRICAL IMPEDANCE FOR CORRECTING THE MEASUREMENT DUE TO EFFECT OF DEPOSITS ON INNER SURFACE OF PIPE WALLS

The present invention relates to a system and method for detection and characterization of deposit formation on pipe walls in process flows and/or measuring the water liquid ratio of the flow.

The present invention relates to a system and method for measuring conditions in a pipe conducting a multiphase fluid flow, multiphase flow typically being a combination of oil, gas and water, but could also be a two-phase gas-liquid flow, e.g. gas and oil, or gas and water. The invention described in the following relates to a multiphase meter using at least density and electrical impedance as primary measurements.

The content of a multi-phase flow may be estimated using electrodes measuring the impedance of the flow, i.e. by finding the permittivity and conductivity of the flow. Several such solutions are known, e.g. as discussed in WO2007/018434, WO2008/085065, WO2005/057142 and U.S. Pat. No. 6,182,504. In all these publications, the measurements are performed by electrodes in contact with the fluid flow, and the quality of the measurements may be diminished by scaling or deposits accumulating on or between the electrodes. WO01/65212A1 discusses the problem with the deposition of materials and other environmental effects on the measurement performance and proposes the use of calibration liquid to compensate for the errors. GB2246866A recites the use of impedance measurements, however, does not go further than to mention that depending upon whether the flow behaves as water-continuous or oil-continuous, the impedance measurements are dominated by the real or the imaginary part, with the other one being negligible. WO94/03802 described a system for measuring electrical characteristics and density in a fluid flow and providing a curve showing the relationship between the measured values.

WO2015/055767 discusses a method for detecting the early onset of deposits on an electrode based multiphase meter but does not advice a method for handling more significant deposits. In WO2015/055767 the aim is to measure a conductive layer if the flow is non-conductive, i.e. oil continuous, or as an alternative an insulating layer if the flow is conductive, and this is performed measuring or monitoring the complex impedance. Also, the measurements are performed for short time steps within an excitation pulse, being able to capture instantaneous changes.

An object of the present invention is to measure a conductive layer when the flow is conductive (or equivalent for capacitance), which will provide a deviation in the performed measurements.

The aim of the present invention is to provide a means for real-time detection and characterization of deposits on the meter body, so that cleaning and, if needed, calibration or adjustments in the measurements may be performed in the interim before cleaning can be done.

It is also an object of the present invention to provide a means for detecting the water liquid fraction of the flow based on measured electrical characteristics and density of the flow, and which is tolerant to density offsets.

In performing measurements in multiphase flows such as water, oil and/or gas flows, it is a well-known problem that deposits may form on the measuring means having contact with the flow and thus affecting the quality of the measurements. The deposits may be removed in different ways or washed out by the flow. The necessity and time between cleaning may vary depending on the conditions and content in the flow. This invention will make it possible to detect if layer has occurred and will provide a measure of the electrical characteristics of the layer as it grows. The invention will therefore also provide a means for correcting the measurement for the effect of the deposit layer.

In the harsh conditions of oil and gas production the measurements are, however, sensitive to a number of variations in the flow, such as variations in fluid properties, e.g. density and conductivity, proportions like water cut and water liquid ratio and flow regimes, as well as being subject to deposits of vax and scale on inside wall of the pipe and on sensors in contact with the flow.

Quite naturally, the measurement performance of the multiphase meter will be affected by any systematic offset occurring in its primary measurements, e.g. in the electrical impedance measurement or in the density measurement.

During normal operation of a multiphase flow meter (MPFM) the inside wall of the meter, including the electrodes for performing the impedance measurements, may be contaminated by substances in the flow. This will act as an offset in the impedance measurement and will lead to erroneous measurements of flow fractions, e.g. water cut, unless corrected. This problem may occur in both conductive and capacitive measurement mode and at times so frequently that cleaning the meters often enough becomes problematic.

Another problem is when there is a systematic offset in the density measurement, which will also lead to erroneous measurements. An offset in the density measurement could as example be introduced by a slight movement of the detector or source of a gamma-based density measurement system.

The objects of the present invention are to solve the problems presented above using a system and method as stated in the accompanying claims.

One aspect of the present invention is thus based on a best fit curve representing both the density and electrical measurements over time so as to eliminate errors caused by short term changes in the flow. The present invention relates to changes occurring over long time spans and are related to the measured density over the same period. This may be over several hours including shorter periods with slugs and variations in the gas fraction without influencing the measurements of the slowly changing deposit layer.

The invention will be described below with reference to the accompanying drawings, illustrating the invention by way of examples.

FIG. 1a,b illustrates the impedance sensor with electrodes and deposit layer

Figure 1A:
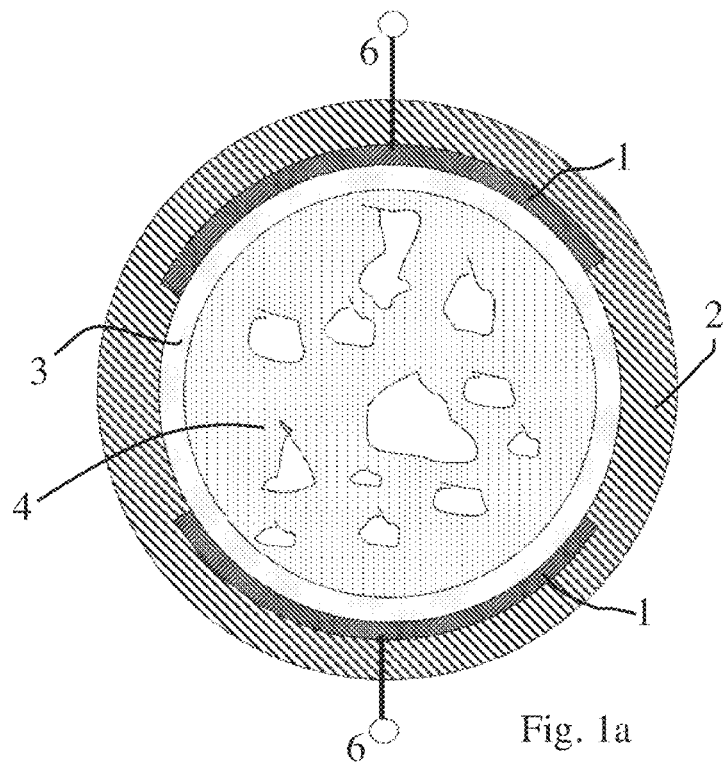

The present invention is illustrated in FIG. 1a including two electrodes 1 on the inner surface of an insulating pipe 2. The insulating pipe 2 may typically be contained in a metal housing (not shown). The pipe contains a multiphase fluid flow 4 illustrated as including liquid with gas bubbles. On the inner wall of the pipe 2 a deposit layer 3 is shown covering the inner wall as well as the electrodes 1. The electrodes are with conductors 6 connected to a measuring instrument (not shown) being able to measure selected electrical characteristics of the flow, and a density measuring instrument (not shown) is also included to measure the density of the fluid 4 being positioned at same position or close to the electrodes, upstream or downstream, so as to measure essentially the same volume of fluid as the electrodes. Thus, the distance depends on how fast the fluid changes and the flow velocity.

The density will typically be measured using gamma rays thus providing a measure of the density in the volume one or more gamma ray passes through, but other means for density measurements may also be used as long as it provides a reliable measure in the volume passing the electrodes.

The illustration shows the use of two electrodes but other configurations including for example six electrodes are possible, for example providing means for detecting deposits on only parts of the inner wall.

Figure 1B:
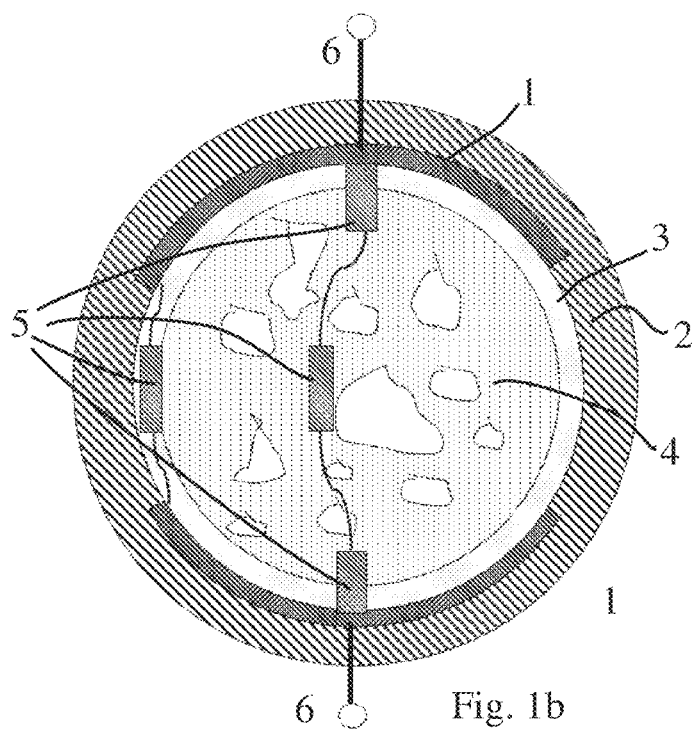

FIG. 1b also shows the electrical characteristics such as the impedance 5 resulting from the flow, and which is the one we want to measure, as well as the impedances related to the deposit layer. The impedances will act as a capacitance in the case of a non-conductive layer/flow otherwise as conductance.

As will be discussed below the electrical characteristic being measured may be resistance, conductance or capacitance depending on the flow conditions and the type of deposits, and these measured impedance values may be converted to electrical property values as conductivity or permittivity for use in the calculations The effect of the layer series impedance will be negligible for a thin capacitive layer in a non-conducting flow, and also for a thin conductive layer in a conducting flow. The parallel impedance will however in both cases result in a significant offset in the measurement of the flow impedance.

One aspect of the present invention will in the following be explained in a case of a conductive flow including determining the effect of a conductive layer on the conductivity measurements of the fluid in a sensor as described above.

Figure 2:
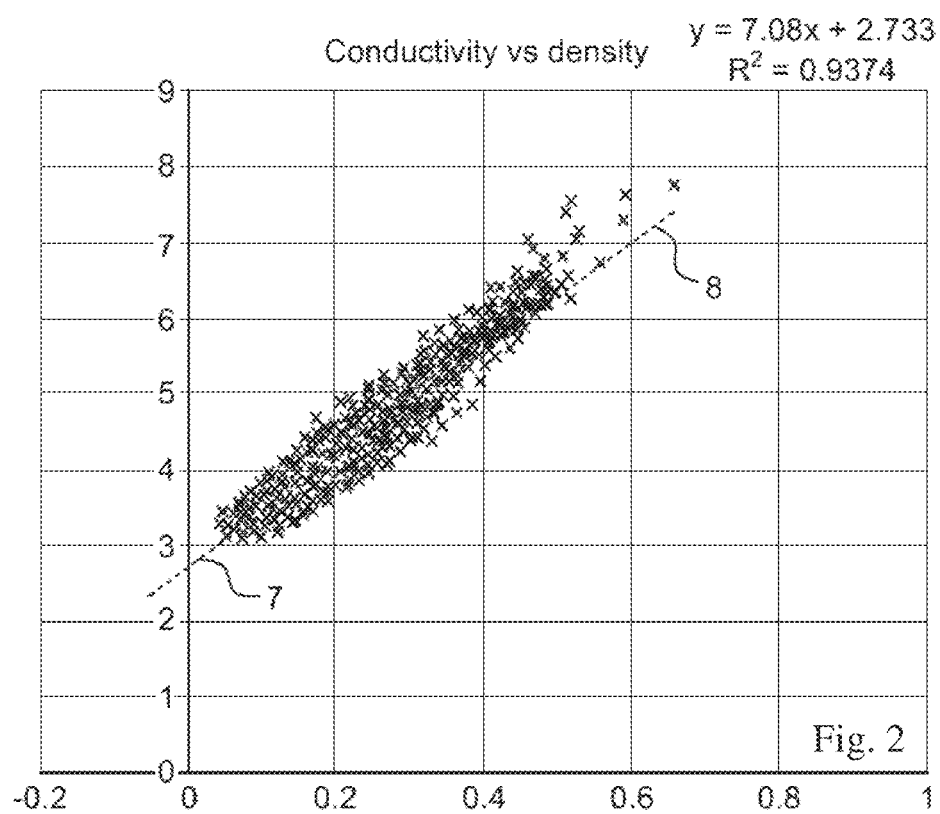
FIG. 2 illustrates a set of sampled conductivity and density data according to the present invention.
Figure 3:
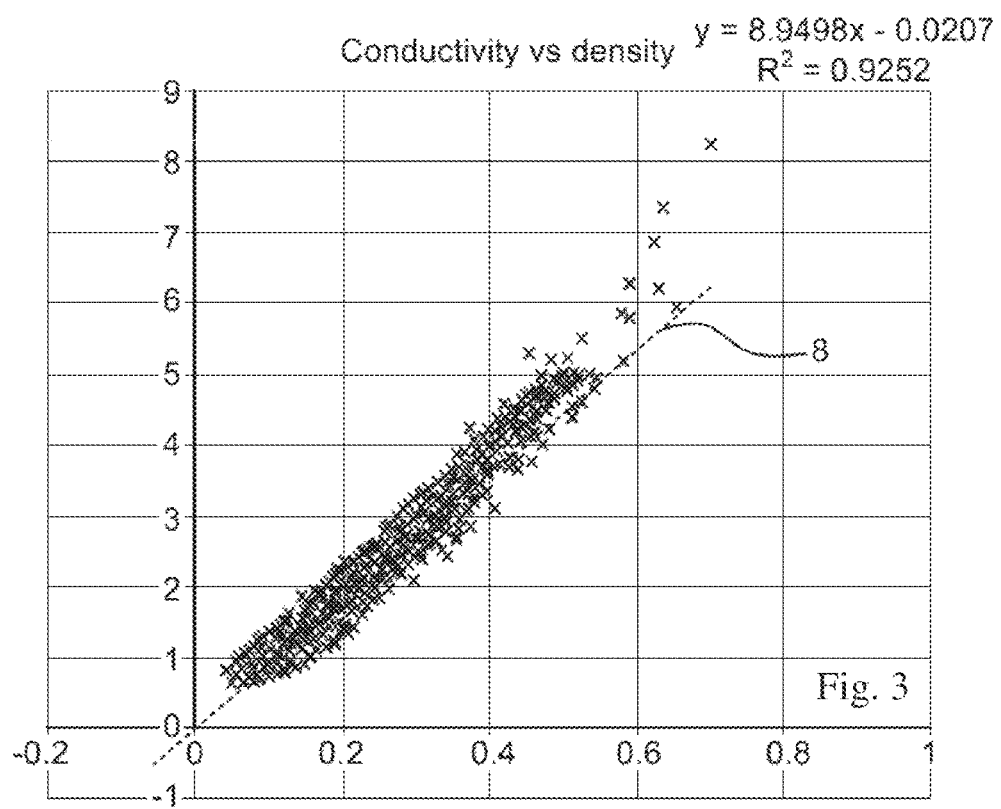
FIG. 3 illustrates the data corresponding to the data in FIG. 2 without contaminations on the sensors.

FIGS. 2 and 3 illustrates conductivity measurements in a flow as a function of density, where a linear relationship is assumed between the density and the conductivity. A line 8 calculated from the measurements shows that the conductivity value 7 for zero density in FIG. 2 is non-zero, which may be interpreted as the conductivity of the deposit layer as given by the offset 7 of this linear function 8. In the example shown in FIG. 2 the offset 7 is approximately 2.7 S/m. In FIG. 3 there is no deposit layer and the conductivity in the case with zero density is zero. This will be discussed in detail below.

When measuring multiphase flow there is a link between the conductivity measurement and density measurement in that both are highly influenced by the gas fraction. Under the assumption of fairly stable fluid properties and water cut, the fluctuations of gas content are therefore by far the biggest contributor to changes in both measurements. These assumptions are not unrealistic, and in fact quite common, when considering an evaluation period of for example a few hours, and in particular in conditions of a slug flow regime. The liquid (oil+water) will then have a constant conductivity and also a constant density.

As both oil and gas can be considered non-conductive, the water fraction of the flow can be calculated from the measured flow conductivity by use of an otherwise known two-component mixing formula, e.g. as described in above-mentioned WO2015/055767 as:

Fw=Water fraction
σ=conductivity (S/m)

$$Fw = \left(\frac{\sigma_{measured}}{\sigma_{water}}\right)^{\frac{2}{3}}$$

so given stationary WLR water fraction is proportional to liquid fraction since:
Fo=Oil fraction
Fl=Liquid fraction=Fo+Fw=1−Fg $$WLR = \frac{Fw}{Fw+Fo} = \frac{Fw}{Fl}$$

$$Fl = \frac{1}{WLR} \times Fw$$

Density measurements can be represented as
Fg=Gas fraction
ρ=density (Kg/m$^3$)

$$\rho_{measured} = \rho_{water} \times Fw + \rho_{Oil} \times Fo + \rho_{gas} \times Fg$$

Using $$\rho_{liquid} = \rho_{water} \times WLR + \rho_{Oil} \times (1-WLR) = \rho_{Oil} + (\rho_{water} - \rho_{Oil}) \times WLR$$

And re-arranging we get $$\rho_{measured} - \rho_{gas} = (\rho_{liquid} - \rho_{gas}) \times Fl$$

Which shows that if we eliminate the gas density the measured density remaining is also linear towards liquid fraction (Fl)

We call this modified density $\rho_{linfrac}$ below.

Then both these values are directly proportional to liquid fraction which we can exploit to detect and correct conductivity measurements. This determination of offset in the conductivity measurement is done, under the assumption of no systematic offset in the density measurements, but it would be trivial to do the opposite.

To estimate the effects of conductive and to some degree insulating layers we are able to do an ordinary linear least square fit (βx+α) between $\rho_{linfrac}$ and Fw and determine the zero crossing a on the x-axis (density).

The R$^2$ value (coefficient of determination) of the fit will give us a very good indicator of how good the fit is (linearity between conductivity and density).

Figure 4:
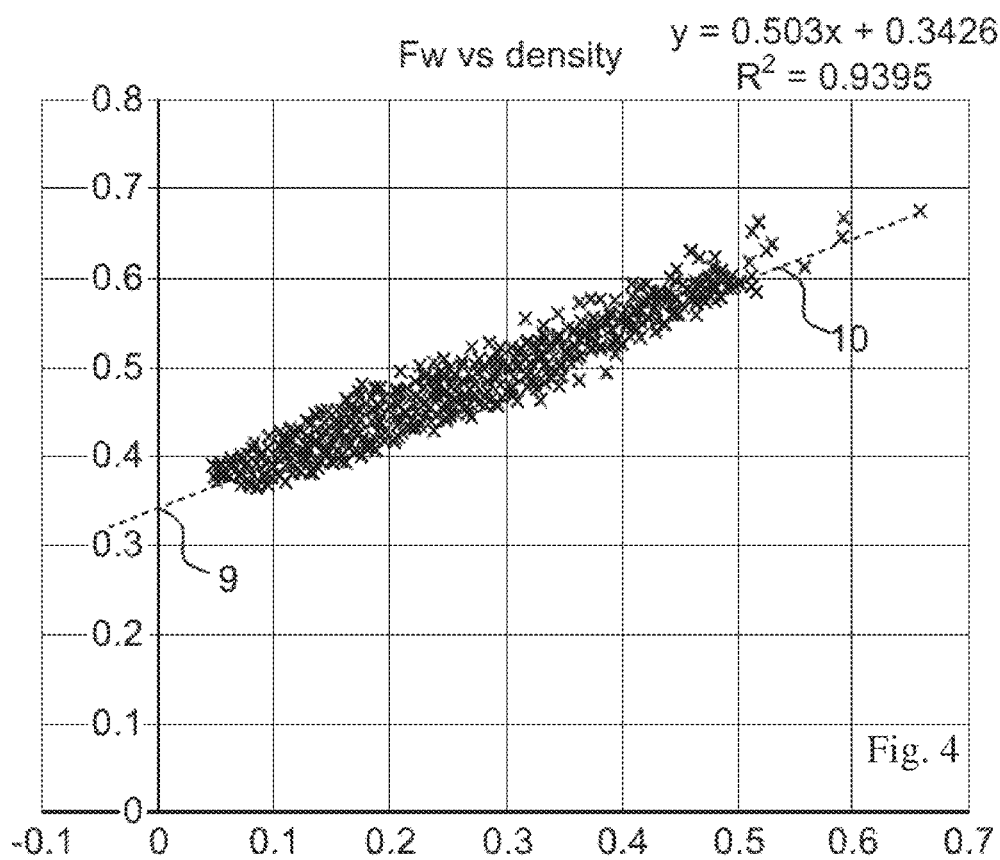
FIG. 4 illustrates s set of sampled water fraction and density data according to the invention.
Figure 5:
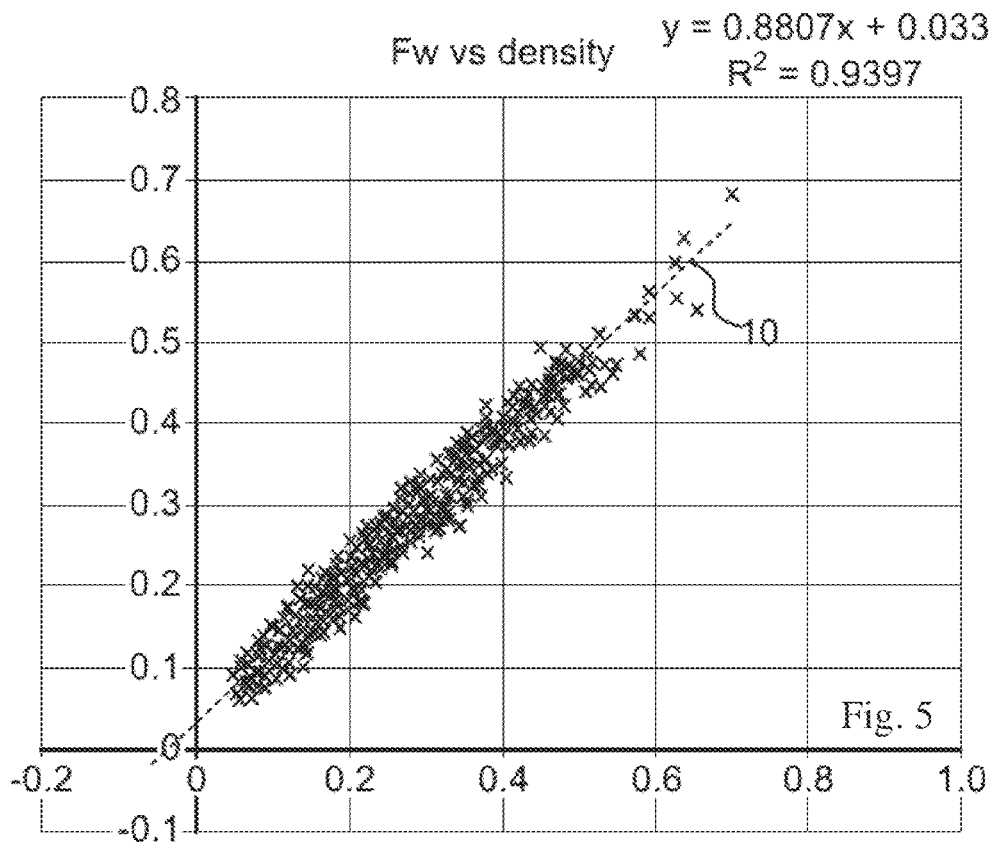
FIG. 5 illustrates the data corresponding to the data in FIG. 3 without contaminations on the sensors.

As is illustrated in FIGS. 4 and 5 the relationship between water fraction Fw and density also provides a linear function 10 with an offset 9 depending on the layer on the pipe wall. In the illustrated case the offset in the water fraction caused by the layer is 0.34.

Using Fw will provide the most exact results since this is directly linear to liquid fraction but estimation directly towards conductivity also yields reasonable results since the ⅔ power is sufficiently linear for the area of interest. It should also be noted that the water conductivity is also not strictly needed to detect conductivity offsets.

The method has been tested on data from field installations with known problem of contaminations and the metered values have shown significant improvements.

The method can also be applied to a non-conductive layer, e.g. a wax layer, when the liquid part of the flow is oil-continuous, and the impedance based multiphase meter therefore operates in capacitance mode, measuring the permittivity of the flow. In this case the capacitance between the electrodes is insignificantly influenced by a thin layer on the electrode itself, but more significantly by the parallel capacitance of a layer on the surface between the electrodes. This layer will then act as a systematic offset in the measured permittivity. The method is the same as above but replacing conductivity by permittivity.

The method can also be used when the systematic offset is found in the density measurement rather than in the impedance measurement. The method is the same as described for the offset in conductivity but replacing conductivity by density.

As stated above it is also an object of the present invention to provide a new water cut algorithm tolerant of density offsets.

The known water cut algorithm used in present instruments conductive measurements is highly sensitive to offset errors on the density measurement system. Any systematic density offset will directly affect the measured water cut. Thus, it is an object of the present invention to provide a method and/or solution improving these measurements.

For a multiphase flow where water cut is largely static over the measurement period fluctuations in density and conductivity is dominated by changes in gas fraction.

Density is given by:

$$\rho = \rho_{liquid} \times Fl + \rho_{gas} \times (1-Fl) = \rho_{gas} + (\rho_{liquid} - \rho_{gas}) \times Fl$$

With $$\rho_{liquid} = \rho_{water} \times WLR + \rho_{Oil} \times (1-WLR) = \rho_{Oil} + (\rho_{water} - \rho_{Oil}) \times WLR$$

This means that there is a linear correlation between density and liquid fraction assuming stationary WLR for the period of interest There is also a linear correlation between liquid fraction and water fraction since: $Fw = WLR \times Fl$ Calculation of water fraction (contrary to water cut) can be done directly from the measured flow conductivity, and is therefore independent of density, so we are able to calculate it separately sample by sample from the measured conductivity.

By collecting a large number of matching density and water fraction samples we are able to do a least square linear fit and from that find the rate of change for water fraction as a function of density change. IE the derivative slope of the curve defining the relationship between water fraction and density, e.g. as illustrated as the slope of the linear curve in FIGS. 2 and 3. This is explained more in detail below.

By expanding the relationships above solving for water fraction as a function of density, forming the first derivate of water fraction by density and finally solving for watercut we arrive at the following equation.

$$WLR = \frac{\beta \times (\rho_{Oil} - \rho_{gas})}{1 - \beta \times (\rho_{water} - \rho_{Oil})}$$

where $\beta$ is the gain factor from the linear fit on the form $\beta x + \alpha$ Since this only depends the relative change of density to relative change of conductivity this algorithm is not affected by constant offsets to the density measurement and can be used to detect errors or even correct meter behavior when needed.

Note that the method described here is most efficient if there is significant change in density during the measurement period since it will not be possible to correlate density to water fraction if the density is static. The method is therefore best suited for wells with intermittent or slugging flow.

It is however easy to check how well the measured density and conductivity correlate by looking at the R-square correlation factor and this will give a strong indication of for the quality of the estimation made by this algorithm.

Calculations:
Fw=Water fraction (Dimensionless)
Fo=Oil fraction (Dimensionless)
Fg=Gas fraction (Dimensionless)
σ=conductivity (S/m)
ρ=density (Kg/m³)
Basic density equation $$\rho = \rho_{water} \times Fw + \rho_{Oil} \times Fo + \rho_{gas} \times Fg$$

Expressed as liquid-gas mix $$\rho = \rho_{liquid} + (\rho_{liquid} - \rho_{gas}) \times Fg \qquad (1)$$

From definitions
Fw+Fo+Fg=1, Fractions sum to one $$WLR = \frac{Fw}{Fw + Fo},$$

Ratio water fraction to liquid fraction
We find $$Fg = 1 - \frac{Fw}{WLR} \qquad (2)$$

Substituting (2) in (1) and simplifying $$\rho = \rho_{liquid} + (\rho_{gas} - \rho_{liquid}) \times \left(1 - \frac{Fw}{WLR}\right) \qquad (3)$$

Assuming stationary WLR $$\rho_{liquid} = \rho_{Oil} + (\rho_{water} - \rho_{Oil}) \times WLR \qquad (4)$$

Substituting (4) in (3) and solving for Fw $$Fw = \frac{WLR \times (\rho - \rho_{gas})}{\rho_{Oil} \times (1 - WLR) + \rho_{water} \times WLR - \rho_{gas}}$$

Differentiating with respect to density $$\frac{dFw}{d\rho} = \frac{WLR}{\rho_{Oil} \times (1 - WLR) + \rho_{water} \times WLR - \rho_{gas}}$$

First derivate (rate of change) corresponds to the gain factor $\beta$ from linear fit $$\beta = \frac{dFw}{d\rho}$$

$$\beta = \frac{WLR}{\rho_{Oil} \times (1 - WLR) + \rho_{water} \times WLR - \rho_{gas}}$$

Solving for WLR $$WLR = \frac{\beta \times (\rho_{Oil} - \rho_{gas})}{1 - \beta \times (\rho_{water} - \rho_{Oil})}$$

As is seen from the discussion above, and especially illustrated in FIGS. 2 and 3, according to one embodiment of the present invention it is possible to obtain two measurements using the same system by measuring the relationship between conductivity between the electrodes and the density of the flow. As the slope of the linear curve calculated from the sampled data provides a measure related to the water cut of the fluid flow and the extension of the line toward the zero density value provides an offset value providing a measure of the deposit layer on the inner surface of the pipe.

Although the relationship between density and conductivity is assumed to be linear this may depend on the measuring situation and method, which may introduce non-linear contributions that may be taken into account when calculating the curve or the derivative/slope of the curve.

To summarize the present invention relates to a measuring system comprising at least two electrodes on the inner wall of a pipe for conducting a multiphase fluid flow, where the pipe may have a deposit layer covering said inner wall. The flow having an essentially constant water liquid ratio (WLR) over a time span. The electrodes are positioned with a chosen distribution on the inner surface of the pipe and being connected to a measuring instrument for measuring the electric characteristics between the electrodes.

The system also comprising a flow density sensor measuring in essentially the same volume as the electrodes, thus providing comparable measurements of the density and the electric characteristic.

The system also includes an analyzing unit in said measuring instrument connected to the density measuring instrument and the electrodes, thus sampling said density and electric measurements at a predetermined rate, and calculating a best fit curve representing the sampled data as a function between the corresponding density and electric measurement data and based on the curve determining the effect of said deposit layer of the electric characteristic. The predetermined rate being chosen depending on the expected short term changes in the flow conditions and expected rate of change in the deposit layer, both being based on previous knowledge of the related flow conditions.

The effect of the deposit layer is found by measuring the conductance or resistance between said two electrodes in the case of a conductive layer and flow, or by measuring the capacitance in the case of a non-conductive layer and flow. For example, the effect of the deposit layer may be an offset in the conductivity measured between said two electrodes.

The electrical property related to said deposit layer is determined from said best fit curve as being the electrical property value corresponding to zero density. Preferably the curve is defined as a linear relationship between the density and the electrical characteristic. The best fit curve is calculated by a least square linear fit.

The time span for performing the measurements may be chosen empirically based on previous measurements of WLR in said flow, by a WLR measuring means monitoring the flow, or be chosen empirically based on previous measurements of fluctuations in gas fraction. The sampling rate is calculated based on the required data accuracy and said time span, so as to avoid short term fluctuation in the flow but provide a sufficiently accurate measurement of changes in the deposite.

According to one aspect of the invention the curve is defined as a linear relationship between the density and the water fraction calculated from the electrical characteristic.

As a supplement or alternative to the deposit layer measurements the analyzing unit of the system may be calculating a best fit linear curve representing the sampled data as a function between the corresponding density and electric measurement data and based on the curve slope determining the water liquid ratio in the flow.

As stated above the linear curve may be calculated by a least square linear fit, the time span is chosen empirically based on previous measurements of WLR in said flow or is defined by a WLR measuring means monitoring the flow. The sampling rate may be calculated based on the required data accuracy and said time span.

The invention also relates to a method for measuring conditions in a pipe including the steps of:
  measuring a chosen electrical characteristic in the flow,
  measuring the density in essentially the same flow volume,
  calculating a curve representing the relationship between the density and the electrical characteristic, preferably the measured impedance represented as conductivity/conductance or permittivity/capacitance,
  also including at least one of the steps of:
calculating the derivative of said curve, indicating the water to liquid ratio of said flow volume, where the curve may be linear and the derivative thus being the slope of the curve, and/or
extrapolating the curve to the value representing zero density, the value of said electric characteristic representing the characteristic of a possible deposit layer on the inner surface of said pipe.

The invention claimed is:

1. A measuring system comprising:
  at least two electrodes on an inner wall of a pipe for conducting a multiphase fluid flow, the pipe having a deposit layer covering the inner wall, the flow having a stable water liquid ratio (WLR) over a time span, the at least two electrodes being positioned on an inner surface of the pipe and being connected to a measuring instrument for measuring electric characteristics in a fluid flow volume between the at least two electrodes;
  a flow density sensor measuring the same fluid flow volume measured by the at least two electrodes; and
  an analyzing unit in the measuring instrument sampling density and electric measurements at a predetermined rate, and calculating a best fit curve representing the sampled data as a function between the corresponding density and electric measurement data and based on the best fit curve determining an effect of the deposit layer.

2. The measuring system according to claim 1, wherein the effect of the deposit layer is a change in a measured conductance or resistance between the at least two electrodes.

3. The measuring system according to claim 1, wherein the effect of the deposit layer is determined from the best fit curve as being an electrical property value corresponding to density at no liquid present.

4. The measuring system according to claim 1, wherein the effect of the deposit layer results from a parallel coupling capacitance between the at least two electrodes represented by the deposit layer.

5. The measuring system according to claim 1, wherein the best fit curve is defined as a linear relationship between the density and the electrical characteristic.

6. The measuring system according to claim 1, wherein the best fit curve is calculated using a least square linear fit method.

7. The measuring system according to claim 1, wherein the time span is chosen empirically based on previous measurements of WLR in the multiphase fluid flow.

8. The measuring system according to claim 1, wherein the time span is defined by using WLR measurements.

9. The measuring system according to claim 1, wherein the sampling rate is calculated based on a required data accuracy and the time span.

10. The system according to claim 1, wherein the best fit curve is defined as a linear relationship between density and water fraction calculated from the electrical characteristic.

11. The measuring system according to claim 1, wherein the time span is chosen empirically based on previous measurements of fluctuations in gas fraction.

12. A measuring system comprising:
at least two electrodes on an inner wall of a pipe for conducting a multiphase fluid flow, the flow having a stable water liquid ratio (WLR) over a time span, the at least two electrodes being positioned on an inner surface of the pipe and being connected to a measuring instrument for measuring electric characteristics in a fluid flow volume between the at least two electrodes;
a flow density sensor measuring the same fluid flow volume measured by the at least two electrodes; and
an analyzing unit in the measuring instrument sampling density and electric measurements at a predetermined rate, and calculating a best fit linear curve representing the sampled data as a function between the corresponding density and electric measurement data and based on a curve slope determining the constant water liquid ratio in the multiphase fluid flow.

13. The measuring system according to claim 12, wherein the best fit linear curve is calculated by using a least square linear fit method.

14. The measuring system according to claim 12, wherein the time span is chosen empirically based on pervious measurements of WLR in the multiphase fluid flow.

15. The measuring system according to claim 12, wherein the time span is defined by using WLR measurements.

16. The measuring system according to claim 12, wherein the sampling rate is calculated based on a required data accuracy and the time span.

17. A method for measuring conditions in a pipe containing a fluid flow, the method comprising :
measuring a chosen electrical characteristic in a volume of the fluid flow;
measuring a density in the same fluid flow volume;
calculating a curve representing a relationship between the density and the electrical characteristic; and
at least one of:
calculating a derivative of the curve, indicating water to liquid ratio of the flow volume; and
extrapolating the curve to a value representing density at no liquid present, the value of the electric characteristic representing the characteristic of a possible deposit layer on an inner surface of the pipe.

18. The method according to claim 17, wherein the electrical characteristic is a change in a conductivity or resistivity of the fluid flow.

19. The method according to claim 17, wherein the curve is assumed to be linear, a slope of which indicates the water to liquid ratio of the flow volume.

* * * * *